(12) United States Patent
Volkenand et al.

(10) Patent No.: US 10,518,062 B2
(45) Date of Patent: Dec. 31, 2019

(54) SUPPORT OR SUPPLY SYSTEM FOR MEDICAL DEVICES

(75) Inventors: Kai Volkenand, Hünfeld (DE); Fritz Ickler, Kirchheim (DE); Stefan Perplies, Hünfeld (DE)

(73) Assignee: ONDAL MEDICAL SYSTEMS GMBH, Hünfeld (DE)

( * ) Notice: Subject to any disclaimer, the term of this patent is extended or adjusted under 35 U.S.C. 154(b) by 299 days.

(21) Appl. No.: 13/824,202

(22) PCT Filed: Nov. 16, 2011

(86) PCT No.: PCT/EP2011/005777
§ 371 (c)(1),
(2), (4) Date: Aug. 26, 2013

(87) PCT Pub. No.: WO2012/065733
PCT Pub. Date: May 24, 2012

(65) Prior Publication Data
US 2013/0338430 A1 Dec. 19, 2013

(30) Foreign Application Priority Data
Nov. 16, 2010 (DE) ........................ 10 2010 051 525

(51) Int. Cl.
| A61M 21/00 | (2006.01) |
| A61M 21/02 | (2006.01) |
| A61G 12/00 | (2006.01) |
| A61G 13/10 | (2006.01) |
| F16M 11/04 | (2006.01) |

(Continued)

(52) U.S. Cl.
CPC ........... *A61M 21/02* (2013.01); *A61G 12/004* (2013.01); *A61G 13/107* (2013.01); *F16M 11/046* (2013.01); *F16M 11/2014* (2013.01); *F16M 13/027* (2013.01)

(58) Field of Classification Search
CPC ....... A61G 10/00; A61G 12/00; A61G 12/002
USPC ......... 600/26–28; 52/27; 248/200, 317, 324; 5/600
See application file for complete search history.

(56) References Cited

U.S. PATENT DOCUMENTS

| 3,556,455 A | 1/1971 | Storm et al. |
| 3,761,631 A * | 9/1973 | Ito ............................ H04S 5/02 |
| | | 381/18 |

(Continued)

FOREIGN PATENT DOCUMENTS

| CN | 101194868 A | 6/2008 |
| DE | 353229 A1 | 3/1987 |

(Continued)

*Primary Examiner* — John P Lacyk
(74) *Attorney, Agent, or Firm* — Seed IP Law Group LLP

(57) ABSTRACT

A console for supplying medical-technical devices in a treatment room has a support frame and several connectors or sockets for medical-technical supply or for withdrawal of gases and/or electrical supply currents, as well as for providing electronic communication paths for medical-technical end devices. The console can incorporate an audio playback system integrated in the support frame for filling the treatment room with predetermined soothing or therapeutic sounds. The support system may be adapted for being mounted to or suspended from a ceiling mount in a treatment room, and can have a support frame having an integrated and medically approved audio playback system.

12 Claims, 3 Drawing Sheets

(51) Int. Cl.
*F16M 11/20* (2006.01)
*F16M 13/02* (2006.01)

(56) References Cited

U.S. PATENT DOCUMENTS

| | | | |
|---|---|---|---|
| 6,349,436 B1 | 2/2002 | Kreuzer | |
| 7,644,898 B2 | 1/2010 | White et al. | |
| 7,770,860 B1 | 8/2010 | Culpepper et al. | |
| 2003/0014817 A1 | 1/2003 | Gallant et al. | |
| 2008/0027574 A1* | 1/2008 | Thomas | A61B 19/00 700/94 |
| 2008/0187155 A1* | 8/2008 | Hou | H04R 1/02 381/300 |
| 2009/0103753 A1* | 4/2009 | Hsu | H04R 1/403 381/307 |
| 2009/0118714 A1 | 5/2009 | Teodorescu | |
| 2010/0223857 A1 | 9/2010 | Sutton et al. | |

FOREIGN PATENT DOCUMENTS

| | | |
|---|---|---|
| DE | 9406348 U1 | 6/1994 |
| DE | 102007002481 A1 | 7/2008 |
| DE | 102007023683 A1 | 11/2008 |
| DE | 102008052491 A1 | 4/2010 |
| EP | 1 647 251 A1 | 4/2006 |
| EP | 1 785 104 A1 | 5/2007 |
| WO | 2004/082553 A2 | 9/2004 |
| WO | 2005/037166 A2 | 4/2005 |
| WO | 2009/018422 A1 | 2/2009 |

\* cited by examiner

SUPPORT OR SUPPLY SYSTEM FOR MEDICAL DEVICES

FIELD OF THE INVENTION

The present invention relates to a console for medical-technical supply in a treatment room, and in particular to a console having several connectors or sockets for medical-technical supply or for withdrawal of gases and/or electrical supply currents for medical-technical end devices.

The console according to the invention is particularly adapted for mounting to or suspending from a support system. Therefore, the invention relates to a medical-technical supply system as well as to a retro-fittable and modular medical support system.

Support systems and supply consoles for medical-technical end devices are frequently used in the clinical field, in particular in hospitals (such as in operating theatres and in intensive care units) and in doctor's offices. In operating theatres, the surgeons and the medical staff work partly under very hard conditions and their performance—as known—has a direct effect on the chances of the corresponding patients concerning a successful recovery. In the meantime, it is furthermore known that a hospital stay, in particular for longer periods of time, has typically a negative effect on the mental condition of the patients which is also considered as not promoting healing, because patients in the hospital often feel lonely and isolated, separated from their familiar environment and partly also from their families and friends. The inventors have therefore spent time on the question as to how such supply and support systems can further support or improve the medical results and the healing chances of the patients.

BRIEF DESCRIPTION OF THE INVENTION

This object is achieved by a console according to claim 1 and/or by a support system according to claim 10. Preferred embodiments of the invention result from the features of the dependent claims.

According to one aspect, the invention provides a console for medical-technical supply in a treatment room, such as in an operating theatre or in an intensive care unit, which console comprises the following features:

- a support frame mountable in a treatment room having several connectors or sockets for medical-technical supply or for withdrawal of gases and/or electrical supply currents, as well as for establishing electronic communication paths for medical-technical end devices, and
- an audio-playback-system integrated in the support frame for playing predetermined soothing and therapeutic sounds in the treatment room, or for filling the treatment room with the predetermined sounds.

The insight that predetermined sounds, such as music, have a soothing or therapeutic effect and can serve for recovery, conservation and promotion of the psychic, physical and mental health, has been implemented by the inventors in the conception of the console according to the invention. Until now there has been a lack of suitable devices or equipment for a secure, hygienic, gentle, and medically approved application of such insight in the stationary and/or ambulant clinical field, in particular in operating theatres and/or in intensive care units. With the present invention, a system has been created from which the patients benefit in two different ways with regard to health and their successful recovery. Firstly, the integrated audio-system can play back one or more records predetermined for the operating surgeon and/or for his medical team, which recordings can then have a particularly calming or concentration-promoting effect on the surgeon and the staff, respectively, so as to improve the physical or medical performance. Secondly, predetermined sounds or music in the stationary clinical field, for example in an intensive care unit, can also have a positive effect on the psychic, physical and mental health of the patients and, thus, counteract the negative mental effect of a hospital stay. Even if a patient is in coma, the predetermined sounds can nevertheless still have a positive subliminal or subconscious effect on the patient.

The predetermined sounds are preferably exactly adapted to or chosen for the patient or the medical staff in order to cause a maximal positive effect. Thereby, the sounds can be a particular favorite piece of music or other predetermined recordings, such as noises of the sea or nature. With the console according to the invention, on the one hand the calming, pain-relieving, relaxing and healing-promoting effect of sounds to the patients can be used, and on the other hand, the calming effect of music to the surgeon can be used, in order to thereby support and possibly improve the medical results and the healing chances.

Preferably, the audio-playback-system of the console according to the invention is a medically approved device comprising several loudspeakers oriented in different directions. Filling the treatment room with sound is preferably designed as filling with background sound. However, the loudspeakers can be integrated in headphones so that the soothing or therapeutic sounds are available for certain listeners only (i.e. those wearing the headphones) in the treatment room.

In a preferred embodiment of the invention, the support frame comprises several modules. The modules are preferably standardized components which share a basic form and which are exchangeable with respect to one another in the support frame. The connectors or sockets are provided at least in one module, preferably in several modules. Furthermore, the audio-system is located in at least one module of the supply console, and preferably in several modules thereof. For example, the audio-system comprises several loudspeakers which are located preferably in several modules of the support frame. The several modules of the support frame are preferably assembled next to one another in one or more rows. Preferably, at least one of the modules comprises a housing which houses parts of the audio-playback-system and which at least partly, preferably substantially completely, surrounds or encloses the parts in a protective manner. The modules lead to a very flexible construction of the console and allow for a cost-effective pre-fabrication or finishing, as well as for a simple mounting and for simple maintenance work. For this purpose, the audio-system is housed in the modules in such a way that the exterior surfaces of the audio-system, such as the loudspeaker modules, can be very easily cleaned or sterilized. In other words, the exterior surfaces of the audio-system in the console according to the invention can be cleaned with disinfectants without affecting the audio-system.

In a preferred embodiment of the invention, the support frame comprises a frame or a core which is adapted for mounting to or suspending from a ceiling mount. The several modules are preferably laterally attached and fixed to the frame or core. Preferably, the support frame has a longitudinal shape and is arranged substantially vertically so that the several modules are arranged one above the other. In a particularly preferred embodiment, a first column being substantially vertically arranged is arranged at one side of the support frame and a second column being substantially vertically arranged is arranged at the opposite side of the support frame, both columns being comprised of modules that are arranged one above the other.

In a preferred embodiment of the invention, the audio-playback-system comprises at least one spot for receiving a sound or music storage medium, such as a diskette, CD, memory stick or similar. Therefore the at least one spot for receiving the sound or music storage medium is designed according to the known storage media. Preferably the audio-playback-system comprises a control unit or a receiving spot for receiving or docking a control unit, with which control unit a user can control or operate playing sounds or music. In this context, the control unit can be a digital playback- or memory-device, such as an "iPod", "iPhone" or an mp3-device, and the console according to the invention can comprise a receiving spot or interface therefor which is designed accordingly—for example as an input for a jack plug so that the control unit can be arbitrarily inserted or removed. Alternatively, the control unit can be integrated in or fixed to one of the modules. If desired, the console can also be equipped with a radio-tuner.

In a preferred embodiment of the invention, the audio-system is programmable by the control unit so as to choose or predetermine the sounds or the music. Preferably, the control unit of the audio-playback-system comprises an audio amplifier or an acoustic irradiation amplifier. Furthermore, the control unit preferably comprises a remote control with which at least the predetermined soothing or therapeutic sounds, the programming and/or the volume can be changed, and the audio-system can be switched on and off.

In a preferred embodiment of the invention, the audio-system has an internet connection via the control unit so as to allow downloading directly from the internet the predetermined sounds or the favorite music pieces. For doing so, the control unit can comprise, for example, a processor and the required software, such as a web browser software. The internet connection can be wireless, for example via a WLAN-connection.

According to a further aspect, the invention provides a support system for medical devices, wherein the support system is adapted for mounting to or suspending from a ceiling mount in a treatment room, and comprises a support frame having an integrated, medically approved audio-playback-system for filling the room with sound. Preferably, the support frame forms part of a console which may be in the form of a supply bridge that is fixedly or movably connected to the ceiling. As a variant, an embodiment of the audio-system as separate unit is possible which can be mounted to another position of the support system, for example mounted separately at a support arm of the support system parallel to the supply console in the operating theatre or the ICU-room. Preferably, the support system comprises a mount for suspending the system from or mounting the system to a ceiling of the treatment room.

Establishing or securely and hygienically positioning a conventional audio-system in an operating theatre or in an intensive care unit has almost been impossible up to now. Furthermore, such an activity could have led to harming patients and the use of such conventional devices would have seemed generally very questionable or inadmissible due to missing medical approval. The integration—according to the invention—of the audio-system in the console or in the support system, however, allows for medical approval and for a secure and hygienic positioning in all areas of the hospital, so that the insight of the soothing or therapeutic sounds can be implemented in the operating theatre and in stationary or ambulant clinical area.

BRIEF DESCRIPTION OF THE DRAWINGS

Further preferred configurations of the invention result from the following description of exemplary embodiments, which is carried out with reference to the attached figures, wherein functionally identical or similar components are designated by the same reference signs.

DESCRIPTION OF THE EXEMPLARY EMBODIMENTS OF THE INVENTION

Figure 1:
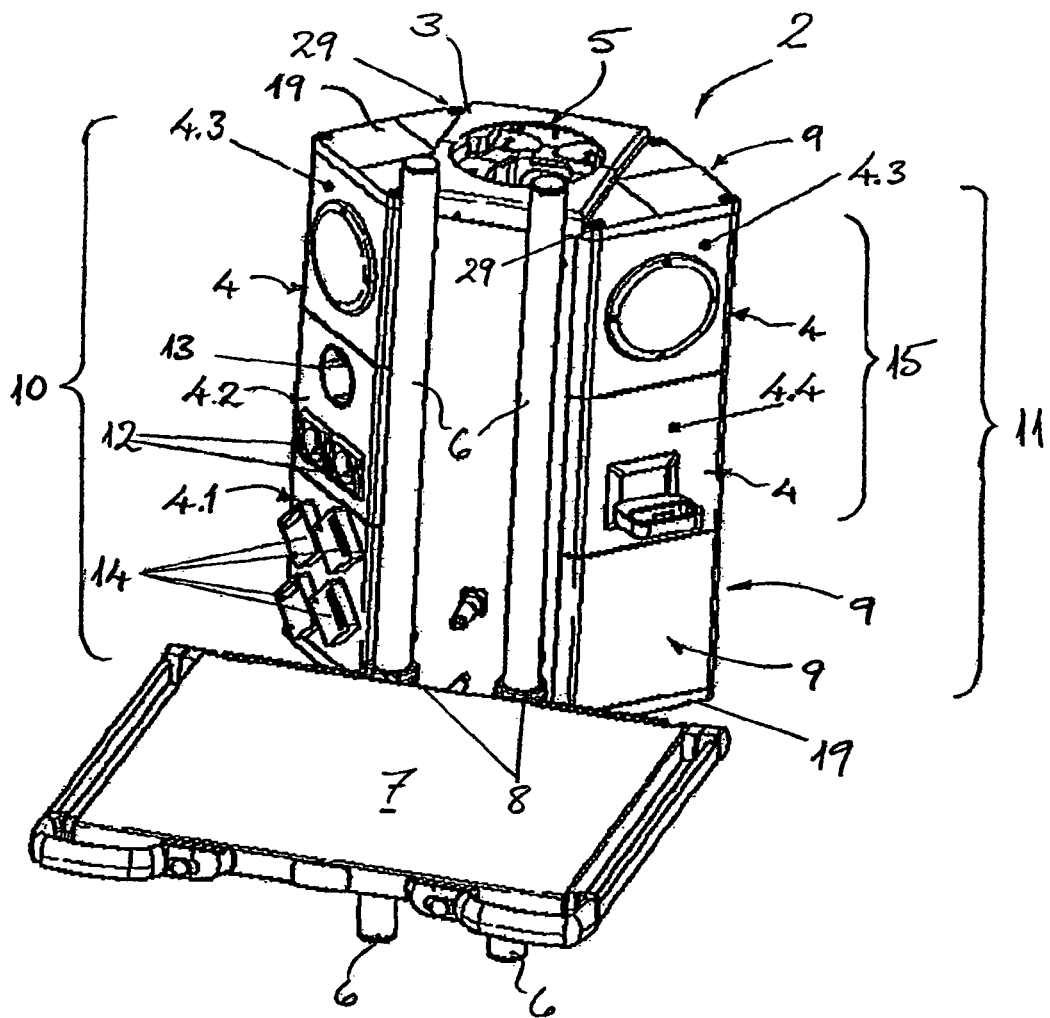
FIG. 1 shows a perspective view of a supply console according to an embodiment of the invention.

FIG. 1 shows a console 1 according to the invention for supplying medical-technical or medical-electrical (ME) end devices (not shown) with gas, electricity and/or communication techniques. The supply console 1 has a support frame 2 which is adapted for mounting to or suspending from the ceiling of a treatment room (for example in an operating theatre or ICU-room (intensive care unit)) in a hospital by means of a ceiling mount. For this purpose the support frame 2 comprises a frame or core 3 and laterally arranged modules 4, which comprise among others sockets or plug connectors for medical-technical supply or for withdrawal of gases and/or electrical supply currents, as well as for establishing electronic communication paths for the ME-end devices. The frame or core 3 of the support frame 2 is centrally arranged, extends substantially vertically between the lateral modules 4, and has a central opening 5 on its upper side, which opening serves as mounting point for fixation to a ceiling mount. Furthermore, the support frame 2 comprises two tubes 6 extending vertically and being fixedly connected with the central frame or core 3 of the support frame 2 and to which a tray 7 for receiving the ME-devices is height-adjustably attached by means of two jaws 8.

With respect to their basic form, the modules 4 are standardized components which are exchangeable with respect to one another. Each of the laterally arranged modules 4 in this exemplary embodiment has a triangular shape and presents two angled lateral surfaces 9, as will be described later in more detail with respect to FIGS. 2 and 3. The modules 4 are arranged at the sides of the support frame 2 in such a way that they form a first column 10 being substantially vertically arranged on a first side of the support frame 2 and a second column 11 being substantially vertically arranged on a second, opposing side of the support frame 2, both columns being comprised of modules 4 that are arranged one above the other.

Even though each module is provided with the same basic form, the modules 4 allow for housing different country-specific variants of power sockets (first sockets 12—all internationally common types of sockets can be integrated), different structural shapes of gas withdrawal sockets (second sockets 13) and different structural shapes of connections of communication electronics (third sockets 14—for example, for a video camera, display etc.). By optionally combining individual modules 4.1, 4.2, a plurality of configuration options is obtained. Considering the latest safety regulations, first, second and third sockets 12, 13, 14 can be optionally provided to the user, pre-assembled in a first or second column 10, 11 (also complete with the console 1 and optionally also with a ceiling mount 30). The modules 4.1, 4.2 consist of a triangular portion of an extruded profile which has the lateral walls 9 of the same width in a right angle. In the portion or in the lateral walls 9, the sockets 12 for current supply and/or the sockets 13 for gas withdrawal and/or sockets 14 for electronic communication techniques are integrated as required and according to use.

According to the invention, the console 1 comprises an audio-playback-system 15 integrated in the support frame 2 for filling the treatment room with predetermined soothing or therapeutic sounds, for example in form of selected or preprogrammed music. In this exemplary embodiment, the audio-system 15 is housed in different modules 4.3, 4.4 of the support frame 2. In other words, the integrated sound system is comprised, as already shown in FIG. 1, of several individual modules 4.3, 4.4 which may be implemented, if necessary, also as combined module.

Figure 2:
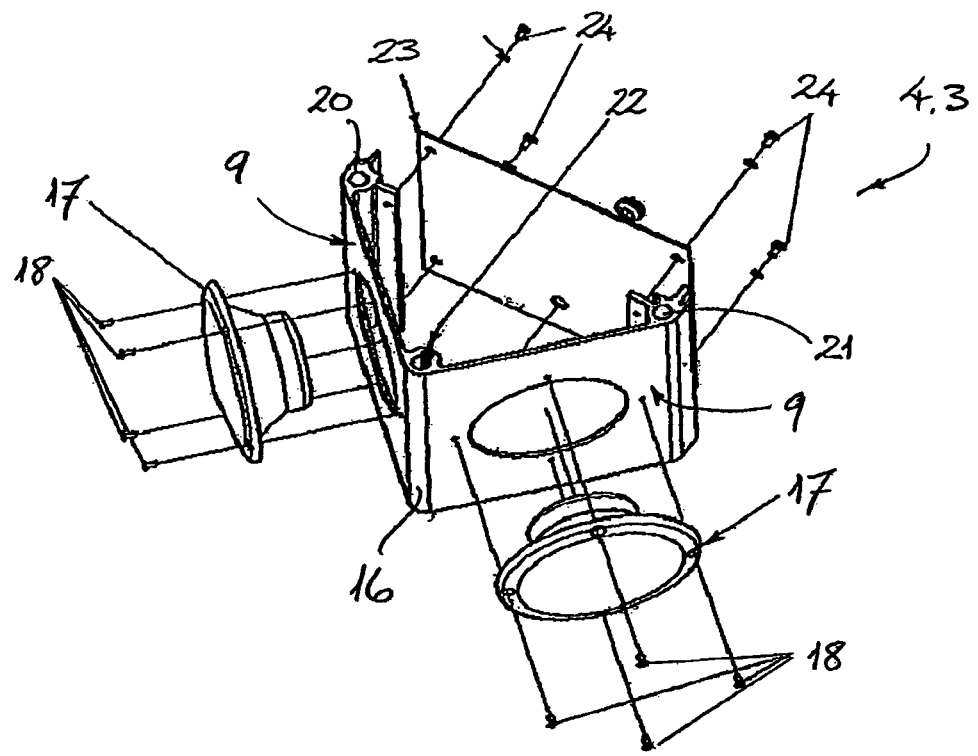
FIG. 2 shows a perspective view of a module of the inventive console in FIG. 1.

A representation of the module 4.3 for playing back acoustic signals, herein as loudspeaker module, is shown in FIG. 2. A triangular base body 16 represents the basis of module 4.3, which base body is adapted for receiving one or several (in this case two) loudspeakers 17. The attachment of each loudspeaker 17 can be carried out by means of force-fit, firmly bonded or positive-locking elements (for example attachment screws 18), similar kinds of attachments or a combination thereof. The base body 16 consists of a portion of an extruded profile which exhibits a first and second lateral wall 9 of the same width with a right angle. When the two loudspeakers 17 are housed in the angled lateral walls 9, they have thus different orientations. A first channel 20 is arranged in an end region of one of the lateral walls 9, and a second channel 21 is arranged in an end region of the other lateral wall 9, and a third channel 22 is arranged in an edge region of the corner, each channel having a circular cross-section. These channels 20-22 serve for respectively receiving a threaded rod for connecting the modules by means of upper and lower cover plates 19 (see FIG. 1). The volume of the base body 16 is closed by means of a cover or sheet metal 23 and the attachment to the base body 16 can be carried out by means of force-fit, firmly bonded or positive-locking elements (for example connections screws 24), similar types of attachment or a combination thereof. Alternatively, the extruded profile and the cover can be implemented combined as base body. The electrical connection of the installed components is realized by means of defined cables which ensure mono-, stereo- or "surround"-playback by means of predefined wiring. Additionally, it is possible connecting a separately suspended loudspeaker (for example in the form of a spherical loudspeaker) in the treatment room.

Figure 3:
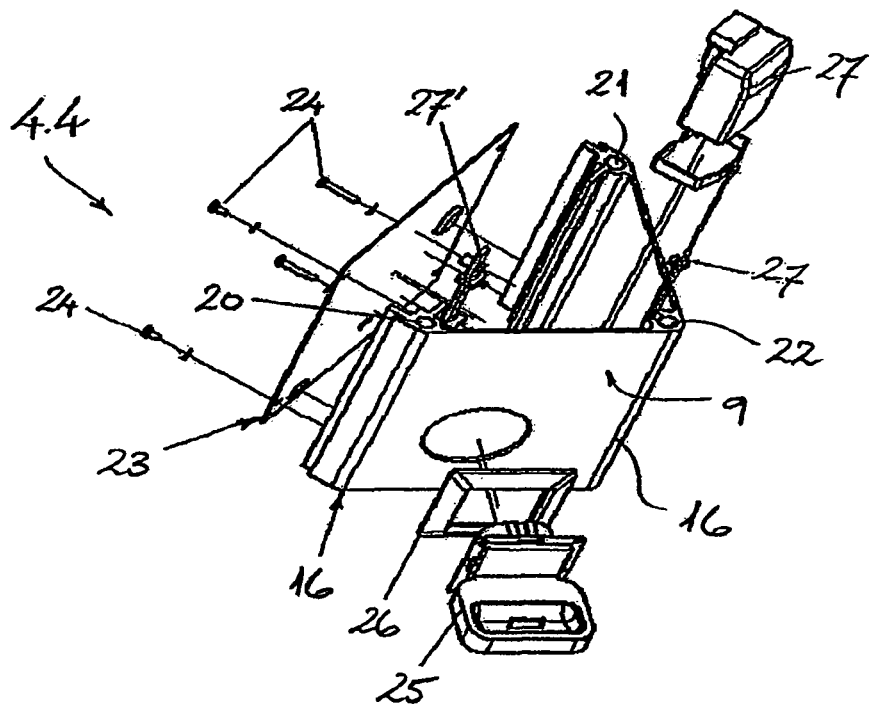
FIG. 3 shows a perspective view of a further module of the inventive console in FIG. 1.

In FIG. 3, a module 4.4 for controlling or amplifying the audio-playback-system 15 is represented, which module 4.4 serves as a docking/amplifier station for playing favorite music pieces. The complete module 4.4 is again composed of a base body 16 and a receiving spot or a docking station 25 with an interface for docking a control unit or a special construction thereof. The receiving spot or docking station 25 can be attached by means of force-fit, firmly bonded or positive-locking elements (for example socket frame 26 in connection with empty boxes), similar kinds of attachment or a combination thereof. For the electrical voltage supply, a power adaptor 27 is installed within the module 4.4, which power adaptor 27 is internally energized by the supply console 1 or by an external voltage supply. The attachment of the power adaptor 27, for example at the base body 16 can be carried out by means of an additional fastening element or by force-fit, firmly bonded or positive-locking elements. The internal wiring 27' is ensured by means of defined cables for electrical signal transmission. Thereby, a mono- or stereo- or a "surround"-operation is possible. An interface for connection with the shown element in FIG. 3 is ensured and enabled by electrical interfaces. Triggering the control device is provided and admissible directly at the element, by means of the remote control F or via other options (for example a "touchscreen").

Separator plates (not shown) between the modules 4, which modules are arranged one above the other, can serve as insertion parts for centering the cut-away extruded profiles with respect to one another. Furthermore, tolerances that result from cutting are thereby masked. The separator plates can also serve for ensuring the gas-tight separation between two modules 4.1-4.4, which are separated from each other by the separator plates and the cover plates 23.

Different equipping configurations of columns 11, 12 can be realized modularly by means of differently equipped modules 4.1-4.4, wherein a system of modules of portions with different heights can be provided. The number of modules 4 can be freely chosen and is independent from the support system for trays 7 and from the device support. Gas and electrical connections, as well as loudspeaker and control units of the audio-system 15 can, if necessary, be mounted on one side (for example, only to the front or to the back). The triangular shape of the modules 4.1-4.4 provide advantages with respect to ergonomics, visual control and laying of cables/pipes or terminal assignment, as well as in view of the operation of the audio-system 15 and the filling of the operating theatre or ICU-room with sound. Moreover, no predefinition with respect to the installation site at the front or at the back or on the left or right side is necessary and the current connections 12, gas connections 13 and communication connections 14 can be installed in an optionally combinable fashion.

One or also two columns 10, 11 mounted to the support frame 2 result in a medical-technical supply unit (console 1) which allows the user to have available medical gases, electrical current supply, communication techniques as well as audio-playback. The configuration or design is determined by the user. The individual modules 4.1-4.4 are equipped and screwed together with the respective sockets 12, 13, 14. Corresponding lines are connected and checked according to quality standards. Differently equipped modules 4.1-4.4 are aligned and mounted with respect to one another with the aid of separator plates. Several modules 4.1-4.4 are combined in a column 10, 11 which is closed on the top and on the bottom by a cover plate 19. Threaded rods including screw connections connect the columns 10, 11 with one another in a positive-locking and force-fit fashion. This mounted unit is mounted to the frame or core 3 of the support frame 2 in order to be subsequently delivered as customer-specific medical-technical supply console 1, completed by tray 7 and, if desired, infusion bar 28 (see FIG. 4). For service or inspection, the columns 10, 11 can swing open by means of a swivel 29.

Figure 4:
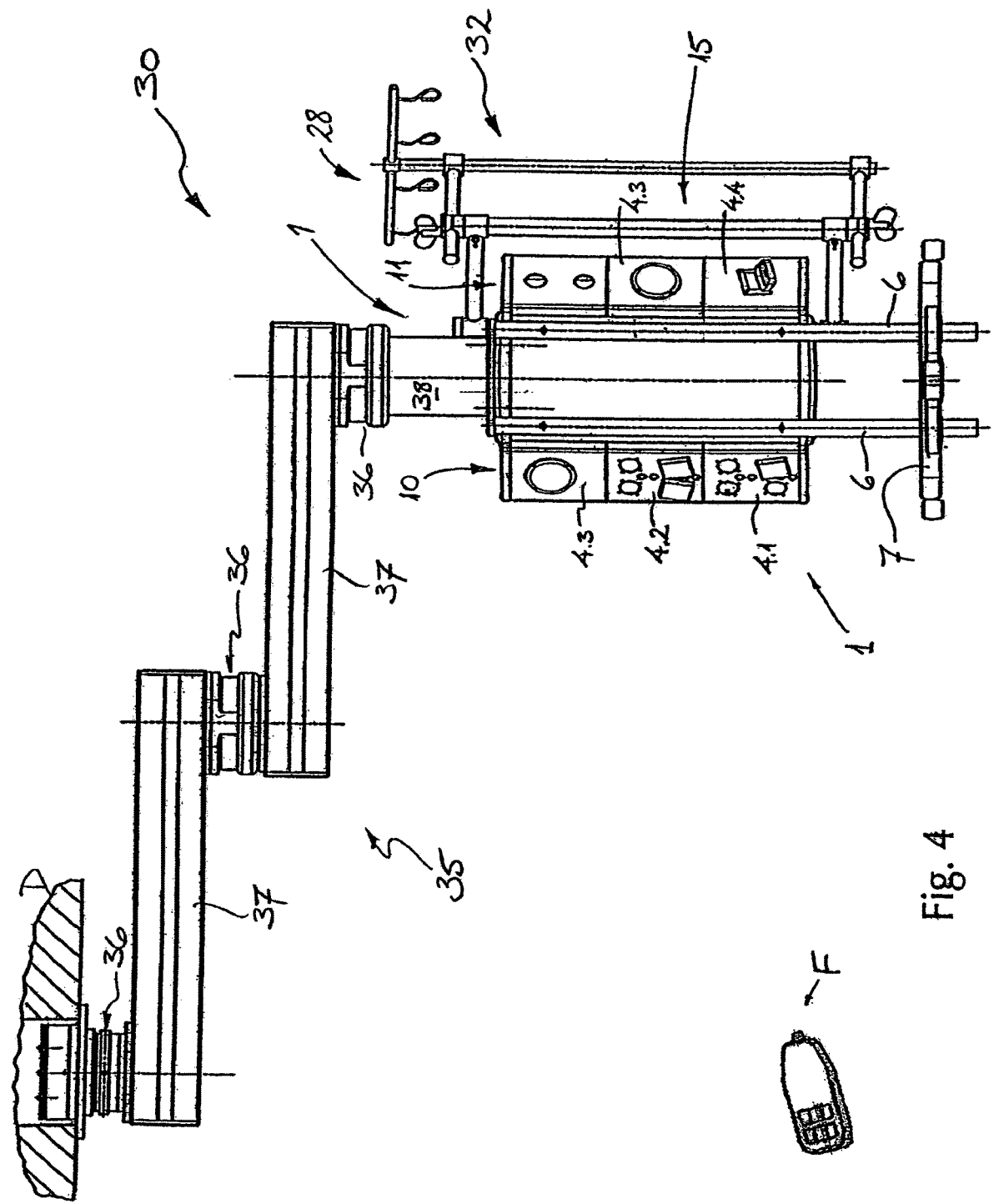
FIG. 4 shows a perspective view of a support system according to an embodiment of the invention.

FIG. 4 shows in a side view a support system 30 according to the invention, wherein the complete console 1 is mounted to a ceiling mount 35, with at least one tray 7 and with a holder 32 for an infusion bar 28. The console 1 is connected to the ceiling mount 35 via the mounting point 5 for positioning in the three-dimensional space (in X-Y-Z-direction). As can be seen from FIG. 4, the supply console 1 can be mounted to ceiling mounts (such as, for example, a boom system or a boom system combined with height-adjustable mounts) or can be implemented as separate column. The ceiling mount or boom system 35 in this exemplary embodiment has three swivels 36, two swiveling arms 37 and a height-adjustable column 38. Also the integration in a supply bridge is possible, which is fixedly or movably connected to the ceiling D. As a further variant, the embodiment of the audio-system 15 as separate unit is possible, which can be mounted to another position of the boom system or support system 35, parallel to the supply console or separately in the operating theatre or ICU-room.

With the present invention, a medically approved audio-system 15 is provided for installation in a medical supply console 1 (which is mounted in an operating theatre or intensive care unit) for playing favorite music pieces (or optionally from radio programs by means of a tuner) for filling the room with background sound during an operation or in the intensive care unit by means of a loudspeaker system being integrated in the supply console and irradiating in four directions, and/or by means of an externally mounted spherical loudspeaker system (irradiating in four directions with "subwoofer") or by means of connected headphones. The audio-system 15 comprises a docking station 25 installed in the console, which is adapted for receiving an iPod or iPhone via a standardized interface or another kind of jack plug connection, which may—as a preferred feature—also comprise a recharging device for the iPod or the iPhone.

The modules 4.3-4.4 of the audio-system 15 consist of a special antibacterial material which is resistant to detergents. They can be operated by an infrared remote control F or manually and have the medical approval so that they are allowed to be applied securely, hygienically and reliably in the patient's environment.

The invention claimed is:

1. A console for medical-technical devices in a treatment room, the console comprising:
    a support frame adapted for mounting in the treatment room and having several connectors or sockets for medical-technical supply, the support frame including:
    several modules, each module including a first panel coupled to a second panel which is oriented at a right angle to the first panel; and
    an audio playback system having a plurality of loudspeakers oriented in different directions and a control unit, the audio playback system integrated in the support frame by a pair of the plurality of loud speakers received in one of the several modules and the control unit received in another one of the several modules which is positioned immediately below the module which receives the pair of the plurality of loudspeakers, the audio playback system configured for filling the treatment room with predetermined soothing or therapeutic sounds, wherein the audio playback system is a medically approved device.

2. A console according to claim 1, wherein the connectors or sockets are provided in at least one of the several modules.

3. A console according to claim 2, wherein the several modules of the support frame are arranged or assembled next to each other in one or several rows.

4. A console according to claim 2 wherein the support frame comprises a frame or a core which is adapted for being mounted to or suspended from a ceiling mount, wherein the several modules are laterally attached or fixed to the frame or core.

5. A console according to claim 2, wherein the support frame exhibits a longitudinal shape and is arranged substantially vertically, wherein the several modules are arranged one above another.

6. A console according to claim 1, wherein a first column being substantially vertically arranged is arranged at one side of the support frame, and wherein a second column being substantially vertically arranged is arranged at an opposite side of the support frame, both columns being comprised of modules that are arranged one above another.

7. A support system for medical devices, wherein the support system is adapted for being mounted to or suspended from a ceiling mount in a treatment room, the support system comprising a support frame having:
    several modules, each module including a first panel coupled to a second panel which is oriented at a right angle to the first panel; and
    an integrated and medically approved audio playback system having a plurality of loudspeakers for playback of predetermined soothing or therapeutic sounds in the treatment room, the audio playback system integrated in the support frame by a pair of the plurality of loud speakers received in one of the several modules and the control unit received in another one of the several modules which is positioned immediately below the module which receives the pair of the plurality of loudspeakers.

8. A support system according to claim 7 having a mount for suspending the system from or mounting the system to a ceiling.

9. A support system according to claim 7, wherein the audio system is adapted for at least one of (a) filling the treatment room with background sound, and
    (b) playing back or emitting the soothing or therapeutic sounds via loudspeakers integrated in headphones, so that the soothing or therapeutic sounds are available for certain listeners only in the treatment room.

10. The console of claim 6 wherein the first column is coupled to the support frame via a first swivel and the second column is coupled to the support frame via s second swivel, the first and second swivels configured to rotatably open and close the respective first and second columns.

11. The console of claim 1 wherein the control unit includes at least one of an audio amplifier or an acoustic irradiation amplifier.

12. The console of claim 1 wherein the control unit includes an acoustic irradiation amplifier.

* * * * *